(12) United States Patent
Lee et al.

(10) Patent No.: US 7,897,366 B2
(45) Date of Patent: Mar. 1, 2011

(54) METHOD FOR SIMULTANEOUS DISPLAY OF TARGET PROTEIN AND COFACTOR REGENERATING ENZYME ON CELL SURFACE

(75) Inventors: Sang Yup Lee, Daejeon (KR); Seung-Hwan Lee, Daejeon (KR)

(73) Assignee: Korea Advanced Institute of Science and Technology, Daejeon (KR)

( * ) Notice: Subject to any disclaimer, the term of this patent is extended or adjusted under 35 U.S.C. 154(b) by 596 days.

(21) Appl. No.: 11/740,390

(22) Filed: Apr. 26, 2007

(65) Prior Publication Data

US 2007/0254368 A1  Nov. 1, 2007

(30) Foreign Application Priority Data

Apr. 27, 2006  (KR) .................. 10-2006-0038023

(51) Int. Cl.
*C12N 15/09* (2006.01)
*C12N 15/70* (2006.01)
(52) U.S. Cl. ..................................... 435/69.1; 435/320.1
(58) Field of Classification Search .................. None
See application file for complete search history.

(56) References Cited

U.S. PATENT DOCUMENTS

| 6,333,175 | B1 * | 12/2001 | Glockshuber et al. | ....... 435/71.2 |
| 2005/0048548 | A1 | 3/2005 | Noren et al. | |

FOREIGN PATENT DOCUMENTS

| KR | 1020000056440 A | 9/2000 |
| KR | 1020020010428 A | 2/2002 |
| KR | 1020050029001 A | 3/2005 |
| WO | 2005123924 | 12/2005 |

OTHER PUBLICATIONS

Bunch et al., Microbiology 143, 185.*
Agterberg et al., "Outer-Membrane PhoE Protein of *Escherichia coli* K-12 as an Exposure Vector: Possibilities and Limitations," Gene, vol. 88, (1990), pp. 37-45.
Charbit et al., "Versatility of a Vector for Expressing Foreign Polypeptides at the Surface of Gram-Negative Bacteria," Gene, vol. 70, (1988), pp. 181-189.
Francisco et al., "Production and Fluorescence-Activated Cell Sorting of *Escherichia coli* Expressing a Functional Antibody Fragment on the External Surface," Proc. Natl. Acad. Sci. USA, vol. 90 (Nov. 1993), pp. 10444-10448.
Hummel et al., "Dehydrogenases for the Synthesis of Chiral Compounds," Eur. J. Biochem., vol. 184, (1989), pp. 1-13.
Jung et al., "Surface Display of *Zymomonas mobilis* Levansucrase by Using the Ice-Nucleation Protein of *Pseudomonas syringae*," Nature Biotechnology, vol. 16, (Jun. 1998), pp. 576-580.
Kjaergaard et al., "Sequestration of Zinc Oxide by Fimbrial Designer Chelators," Applied and Environmental Microbiology, vol. 66, No. 1, (Jan. 2000), pp. 10-14.
Kula et al., "Dehydrogenases in the Synthesis of Chiral Compounds," Stereoselective Biocatalysts, ed. Ramesh N. Patel, Bristol-Myers Squibb Pharmaceutical Research Institute, pp. 839-866, 2000.
Lang et al., "Characterization of Adhesive Epitopes with the OmpS Display System," Eur. J. Biochem., vol. 267, (2000), pp. 163-170.
Lee et al., "Microbial Cell-Surface Display," Trends in Biotechnology, vol. 21, No. 1, (Jan. 2003), pp. 45-52.
Lee et al., "Display of Bacterial Lipase on the *Escherichia coli* Cell Surface by Using FadL as an Anchoring Motif and Use of the Enzyme in Enantioselective Biocatalysts," Applied and Environmental Microbiology, vol. 70, No. 9, (Sep. 2004), pp. 5074-5080.
Lee et al., "Enantioselective Resolution of Racemic Compounds by Cell Surface Displayed Lipase," Enzyme and Microbial Technology, vol. 35, (2004), pp. 429-436.
Richins et al., "Biodegradation of Organophoshorus Pesticides by Surface-Expressed Organophosphorus Hydrolase," Nature Biotechnology, vol. 15, (Oct. 1997), pp. 984-987.
Soura et al., "Metalloadsorption by *Escherichia coli* Cells Displaying Yeast and Mammalian Metallothioneins Anchored to the Outer Membrane Protein LamB," Journal of Bacteriology, vol. 180, No. 9, (May 1998), pp. 2280-2284.
Stahl et al., "Bacterial Surface Display: Trends and Progress," TIBTECH, vol. 15, (May 1997), pp. 185-192.
Yun et al., "Stereospecific Synthesis of (R)-2-Hydroxy Carboxylic Acids Using Recombinant *E. coli* BL21 Overexpressing YiaE from *Escherichia coli* K12 adn Glucose Dehydrogenase from *Bacillus subtilis*," Biotechnol. Prog., vol. 21, (2005), pp. 366-371.

* cited by examiner

*Primary Examiner* — Nancy Vogel
(74) *Attorney, Agent, or Firm* — Tristan A. Fuierer; Moore & Van Allen, PLLC; Andrew D. Gerschutz (57) ABSTRACT

The present invention relates to a method for simultaneously surface expressing a target protein using a cofactor and an enzyme regenerating the cofactor on the cell surface. According to the present invention, it is possible to provide a microorganism capable of simultaneously surface expressing a target protein using a cofactor to transform a biochemical material at a high efficiency and an enzyme generating the cofactor without adding an expensive cofactor in a large amount.

12 Claims, 2 Drawing Sheets

SEQUENCE LISTING

```
<160> NUMBER OF SEQ ID NOS: 12

<210> SEQ ID NO 1
<211> LENGTH: 28
<212> TYPE: DNA
<213> ORGANISM: Artificial
<220> FEATURE:
<223> OTHER INFORMATION: Synthetic Construct

<400> SEQUENCE: 1
cgagctcatg aaagttaaag tactgtcc                                        28

<210> SEQ ID NO 2
<211> LENGTH: 33
<212> TYPE: DNA
<213> ORGANISM: Artificial
<220> FEATURE:
<223> OTHER INFORMATION: Synthetic Construct

<400> SEQUENCE: 2
ggctctagag ccacgaccgt tgttagttac gcc                                  33

<210> SEQ ID NO 3
<211> LENGTH: 30
<212> TYPE: DNA
<213> ORGANISM: Artificial
<220> FEATURE:
<223> OTHER INFORMATION: Synthetic Construct

<400> SEQUENCE: 3
ggctctagag ccacgaccca ggtttttacc                                      30

<210> SEQ ID NO 4
<211> LENGTH: 1104
<212> TYPE: DNA
<213> ORGANISM: Escherichia coli

<400> SEQUENCE: 4
atgaaagtta aagtactgtc cctcctggtc ccagctctgc tggtagcagg cgcagcaaac      60
gctgctgaag tttacaacaa agacggcaac aaattagatc tgtacggtaa agtagacggc     120
ctgcactatt tctctgacaa caaagatgta gatggcgacc agacctacat gcgtcttggc     180
```

-continued

```
ttcaaaggtg aaactcaggt tactgaccag ctgaccggtt acggccagtg ggaatatcag     240
atccagggca acagcgctga aaacgaaaac aactcctgga cccgtgtggc attcgcaggt     300
ctgaaattcc aggatgtggg ttctttcgac tacggtcgta actacggcgt tgtttatgac     360
gtaacttcct ggaccgacgt actgccagaa ttcggtggtg acacctacgg ttctgacaac     420
ttcatgcagc agcgtggtaa cggcttcgcg acctaccgta acactgactt cttcggtctg     480
gttgacggcc tgaactttgc tgttcagtac cagggtaaaa acggcaaccc atctggtgaa     540
ggctttacta gtggcgtaac taacaacggt cgtgacgcac tgcgtcaaaa cggcgacggc     600
gtcggcggtt ctatcactta tgattacgaa ggtttcggta cggtggtgc gatctccagc     660 tccaaacgta ctgatgctca gaacaccgct gcttacatcg taacggcga ccgtgctgaa     720 acctacactg gtggtctgaa atacgacgct aacaacatct acctggctgc tcagtacacc     780
cagacctaca acgcaactcg cgtaggttcc ctgggttggg cgaacaaagc acagaacttc     840
gaagctgttg ctcagtacca gttcgacttc ggtctgcgtc cgtccctggc ttacctgcag     900
tctaaaggta aaacctggg tcgtggctac gacgacgaag atatcctgaa atatgttgat     960
gttggtgcta cctactactt caacaaaaac atgtccacct acgttgacta caaaatcaac    1020
ctgctggacg acaaccagtt cactcgtgac gctggcatca acactgataa catcgtagct    1080
ctgggtctgg tttaccagtt ctaa                                           1104

<210> SEQ ID NO 5
<211> LENGTH: 29
<212> TYPE: DNA
<213> ORGANISM: Artificial
<220> FEATURE:
<223> OTHER INFORMATION: Synthetic Construct

<400> SEQUENCE: 5
gctctagaat gaaggttgta ctagttctc                                        29

<210> SEQ ID NO 6
<211> LENGTH: 27
<212> TYPE: DNA
<213> ORGANISM: Artificial
<220> FEATURE:
<223> OTHER INFORMATION: Synthetic Construct

<400> SEQUENCE: 6
cccaagcttt tatttgtcgg caccgta                                          27

<210> SEQ ID NO 7
<211> LENGTH: 1089
<212> TYPE: DNA
<213> ORGANISM: Hanseniella sp. 'jcrjws1'

<400> SEQUENCE: 7
atgaaggttg tactagttct ctacgacgca ggaaaacacg cccaagacga ggaaagactc      60
tacggttgca ctgaaaacgc ccttggtatc agggactggc tcgagaagca gggccacgac    120
gtcgttgtca ccagtgacaa ggaggggcag aactctgtgc tcgagaagaa catctcggac    180
gcagatgtca tcatctccac tccttttccac ccagcataca tcaccaagga gagaatcgac    240
aaggccaaga agctcaagct actggtggtt gccggagtgg gatccgacca catcgacctt    300
gactacatca accagtccgg cagagacatt tctgtgctgg aggtgaccgg ttcgaacgtc    360
gtttcggttg ccgagcacgt tgtgatgacg atgctggtgc tggtgaggaa ctttgttcct    420
gctcacgagc agatcatctc tggcggctgg aacgtggccg agatcgccaa ggactccttc    480
```

```
gacatcgagg gcaaggtcat tgccaccatc ggagcaggca gaatcggcta ccgtgtgctg    540
gagagacttg tggccttcaa ccctaaggag ctgctctact acgactacca gtcgctgtcg    600
aaagaggcgg aggagaaagt cggcgcccgc agagtccacg acatcaagga gctggttgcc    660
caggccgaca ttgtcacgat caactgtcca ctgcacgccg gctcgaaggg cctggtgaac    720
gcagagctgc tcaagcactt caagaagggc gcctggctcg tcaacaccgc cagaggtgcc    780
atctgcgtgg ccgaggacgt tgcagccgcc gtcaagagcg acagcttag aggatacggt     840 ggagacgtgt ggttcccaca gccagctcca aaggaccacc catggagatc catggccaac    900
aagtacggtg ctggcaatgc catgactccg cactactcgg gctctgtcat tgacgcccag    960
gtcagatacg cgcagggcac caagaacatc ctggagtcgt tcttcactca gaagttcgac   1020
tacaggcccc aggacatcat tctgctgaac ggcaagtaca agaccaagtc gtacggtgcc   1080
gacaaatga                                                            1089

<210> SEQ ID NO 8
<211> LENGTH: 56
<212> TYPE: DNA
<213> ORGANISM: Artificial
<220> FEATURE:
<223> OTHER INFORMATION: Synthetic Construct

<400> SEQUENCE: 8
cccaagcttt tatttgtcat cgtcgcttcc ttgtagtctt tgtcggcacc gtacga         56

<210> SEQ ID NO 9
<211> LENGTH: 28
<212> TYPE: DNA
<213> ORGANISM: Artificial
<220> FEATURE:
<223> OTHER INFORMATION: Synthetic Construct

<400> SEQUENCE: 9
gctctagaat gaaactcgcc gtttatag                                        28

<210> SEQ ID NO 10
<211> LENGTH: 29
<212> TYPE: DNA
<213> ORGANISM: Artificial
<220> FEATURE:
<223> OTHER INFORMATION: Synthetic Construct

<400> SEQUENCE: 10
cccaagcttt taaaccagtt cgttcgggc                                       29

<210> SEQ ID NO 11
<211> LENGTH: 990
<212> TYPE: DNA
<213> ORGANISM: Escherichia coli

<400> SEQUENCE: 11
atgaaactcg ccgtttatag cacaaaacag tacgacaaga agtacctgca acaggtgaac     60
gagtcctttg gctttgagct ggaattttt gactttctgc tgacggaaaa aaccgctaaa     120
actgccaatg gctgcgaagc ggtatgtatt ttcgtaaacg atgacggcag ccgcccggtg    180
ctggaagagc tgaaaaagca cggcgttaaa tatatcgccc tgcgctgtgc cggtttcaat    240
aacgtcgacc ttgacgcggc aaaagaactg gggctgaaag tagtccgtgt tccagcctat    300
gatccagagg ccgttgctga acacgccatc ggtatgatga tgacgctgaa ccgccgtatt    360
caccgcgcgt atcagcgtac ccgtgatgct aacttctctc tggaaggtct gaccggcttt    420
```

```
actatgtatg gcaaaacggc aggcgttatc ggtaccggta aaatcggtgt ggcgatgctg    480
cgcattctga aaggttttgg tatgcgtctg ctggcgttcg atccgtatcc aagtgcagcg    540
gcgctggaac tcggtgtgga gtatgtcgat ctgccaaccc tgttctctga atcagacgtt    600
atctctctgc actgcccgct gacaccggaa aactatcatc tgttgaacga agccgccttc    660
gaacagatga aaaatggcgt gatgatcgtc aataccagtc gcggtgcatt gattgattct    720
caggcagcaa ttgaagcgct gaaaaatcag aaaattggtt cgttgggtat ggacgtgtat    780
gagaacgaac gcgatctatt ctttgaagat aaatccaacg acgtgatcca ggatgacgta    840
ttccgtcgcc tgtctgcctg ccacaacgtg ctgtttaccg ggcaccaggc attcctgaca    900
gcagaagctc tgaccagtat ttctcagact acgctgcaaa acttaagcaa tctggaaaaa    960
ggcgaaacct gcccgaacga actggtttaa                                    990

<210> SEQ ID NO 12
<211> LENGTH: 50
<212> TYPE: DNA
<213> ORGANISM: Artificial
<220> FEATURE:
<223> OTHER INFORMATION: Synthetic Construct

<400> SEQUENCE: 12
cccaagcttt taatggtgat gatggtgatg aaccagttcg ttcgggcagg              50
```

METHOD FOR SIMULTANEOUS DISPLAY OF TARGET PROTEIN AND COFACTOR REGENERATING ENZYME ON CELL SURFACE

CROSS-REFERENCE TO RELATED APPLICATION

This application claims priority under 35 USC 119 of Korean Patent Application No. 10-2006-0038023 filed Apr. 27, 2006.

BACKGROUND OF THE INVENTION

1. Field of the Invention

The present invention relates to a method for simultaneously surface expressing a target protein using a cofactor and an enzyme regenerating the cofactor on the cell surface.

2. Background of the Related Art

Cell surface display is a technology to express a protein or peptide fused with a proper anchoring motif on the surface of gram-negative and gram-positive bacteria, fungi, yeast, animal cells (Lee, S. Y. et al., *Trends Biotechnol.*, 21:4552, 2003). According to the first cell surface display technology in the 1980's, a peptide or a small protein is fused with pIII, a filamentous phage, using a phage with relatively simple surface to express the peptide or protein on the surface of the phase, and thus it was called surface expression system. The cell surface display using a phage was used in screening of antibodies or screening of epitope, high-affinity ligand and the like. However, it has a problem in that the size of proteins that can be expressed on the phage surface is limited. As an alternative method, cell surface display using bacteria was developed. According to this technology, the surface protein of a microorganism such as bacteria or yeast is used as a surface anchoring motif to stably express a foreign protein on the surface of the microorganism.

In order to successively accomplish the cell surface display in microorganisms, firstly, it is necessary to select a surface anchoring motif for stably and effectively delivering the foreign protein to be expressed to the cell surface. The surface anchoring motif which has been used in *E. coli* so far includes membrane proteins, spore proteins, lipoproteins, autotransporters and S-layer proteins of surface appendage. Among them, the membrane proteins are widely used as a surface anchoring motif because they have a loop structure which can pass through the cell membrane due to three dimensional structures thereof and thus can provide fusion sites for expression of various proteins.

Particularly, the cell membrane proteins such as OmpA, OmpS, LamB, OprF, PhoE and the like are used in the expression of peptides, antibodies, domains, receptors and the like, having a relatively small molecular weight (Agterberg, M. et al., gene, 88:37, 1990; Lang, H., et al., *Eur. J. Bacteriol.*, 267:163, 2000). Since the C-terminal and N-terminal of the inserted foreign protein should be positioned stereochemically close to each other, if the protein is big, the stability of the protein is low. In practice, when a foreign protein consisting of over 50 to 60 amino acids is inserted to LamB or PhoE, a stable protein cannot be formed due to stereochemical restriction. Also, when an outer membrane porin protein of *E. coli* is limitedly used in the expression of, not the protein of maximum 150 amino acids but an epitope or a metal binding motif (Stahl, S. et al., *Trends Biotechnol.*, 15:185, 1997; Kjaergaad, K. et al., *Appl. Environ. Microbiol.*, 66:10, 2000). Recently, stable surface display of enzymes with relatively large molecular weight using membrane protein FadL, OmpC, ice nucleation protein and the like has been reported (Jung, H. C. et al., *Nature Biotechnol.* 16:576, 1998; Lee, S. H. et al., *Appl. Environ. Microbiol.* 70:5074, 2004; Lee, S. H. et al., *Enzyme Microbial Technol.* 35:429, 2004).

The application range of cell surface display employing secretion system of bacteria is very wide. According to the protein or peptide expressed on the surface, it can be used for various purposes. It is possible to perform the screening of peptides, antibodies, receptors and the like in a simple way by expressing a specific protein on the surface (Francisco, J. A. R. et al., *Proc. Natl. Acad. USA.*, 91:10444, 1993), and to produce a live vaccine showing strong immune response by expressing antigen epitope on the cell surface. Also, specific enzymes needed in fine chemistry, agricultural medicines and medicines can be used as a whole cell live catalyst by expression on the cell surface and proteins which can decompose pollutants or absorb metal ions can be used in bioremediation through surface expression (Charbit, A. et al., *Gene.*, 70:181, 1988; Sousa, C. et al., *J. Bacteriol.*, 180:2280, 1998; Richins, R. et al., *Nat. Biotechnol.*, 15:984, 1997).

Various enzymes are used in the process for producing substances with optical activity. Researches to produce substances with optical activity using the cell surface display system have been actively conducted. In this case, an enzyme having stereoselectivity is expressed on the cell surface and used as a whole cell catalyst (WO 2005/123924). When a hydrolase is employed in optical resolution after surface display, maximum theoretical yield is only 50%. However, unlike the hydrolase, an oxidoreductase is able to convert a prochiral substance to a substance with optical activity to have a theoretical yield of 100% and thus, attracts attention in various fields such as pharmaceutics, fine chemistry, and food and cosmetic industries (Hummel and Kula, *Eur J Biochem* 184:1, 1989). However, since it requires expensive materials such as NAD, NADP and FAD as a cofactor of the reaction, it is hardly applicable in the industry.

In order to solve this problem, a method comprising overexpressing an enzyme capable of regenerating a cofactor in a microorganism such as *E. coli* and using the microorganism as a whole cell enzyme or purifying the over-expressed enzyme and regenerating the cofactor has been studied (Yun, H. et al., *Biotechnol. Prog.*, 21:366-371, 2005; Kula, M. R. and Kragl, U., Dehydrogenases in the synthesis of chiral compounds, in Stereoselective biocatalysis, 839-866, Ed: Patel, R. N. Marcel Dekker, Inc. New York, 2000). However, it has disadvantages in that the cofactor should pass through the microorganism to be delivered to the enzyme and thus, the efficiency of the process is low and an additional process is needed for purification of the over-expressed enzyme.

Therefore, the present inventors have found that it is possible to transform the biochemical material at a high efficiency without adding an expensive cofactor in a large amount by simultaneously surface-expressing the target protein using a cofactor and an enzyme regenerating the cofactor and using the cell in the transformation of a biochemical material. Based on the above finding, the present invention has been completed.

SUMMARY OF THE INVENTION

In one aspect, the present invention relates to a method for simultaneously expressing a cofactor regenerating enzyme and a target protein using the cofactor on the cell surface comprising the steps of: (a) preparing a recombinant vector for regenerating the cofactor comprising DNA having a gene encoding an enzyme for regenerating the cofactor linked to a gene encoding a surface anchoring motif so that the enzyme regenerating the cofactor is expressed in the form fused with the surface anchoring motif; (b) preparing a recombinant vector for expressing the target protein comprising DNA having a gene encoding the target protein linked to a gene encoding the surface anchoring motif so that the target protein using the cofactor is expressed in the form fused with the surface anchoring motif; (c) transforming the recombinant vector for expressing the target protein and the recombinant vector for regenerating the cofactor into a host cell; and (d) surface expressing the enzyme regenerating the cofactor and the target protein by culturing the transformed cells.

In another aspect, the present invention relates to a cell transformed with a recombinant vector for regenerating a cofactor, comprising DNA having a gene encoding an enzyme regenerating the cofactor linked to a gene encoding a surface anchoring motif and a recombinant vector for expressing a target protein comprising DNA having a gene encoding the target protein using the cofactor linked to a gene encoding a surface anchoring motif, in which the enzyme regenerating the cofactor and the target protein using the cofactor are simultaneously surface expressed, and a method for biotransforming a biochemical material comprising carrying out a reaction catalyzed by the target protein using the cell.

The above and other objects, features and embodiments of the present invention will be more clearly understood from the following detailed description and the accompanying claims.

DETAILED DESCRIPTION OF THE INVENTION, AND PREFERRED EMBODIMENT THEREOF

The present invention relates to a method for simultaneously expressing a target protein using a cofactor and an enzyme regenerating the cofactor without adding an expensive cofactor in a large amount, in which the target protein is capable of transforming a biochemical material at a high efficiency.

According to the present invention, a recombinant vector for expressing a gene encoding a target protein using a cofactor and a gene encoding a surface anchoring motif in the form of a fusion protein and a recombinant vector for cofactor regeneration, which express a gene encoding the cofactor regenerating enzyme and a gene encoding a surface anchoring motif in the form of a fusion protein. Moreover, the recombinant vector for expressing the target protein and the recombinant vector for regenerating the cofactor are transformed into a cell surface expressing a surface anchoring motif to prepare a recombinant cell surface expressing the target protein and the cofactor regenerating enzyme.

When a microorganism surface expressing the target protein and the cofactor regenerating enzyme is used in place of a catalase enzyme in the transformation of a biochemical material essentially needing a cofactor, the used cofactor is continuously regenerated by the surface-expressed enzyme for cofactor regeneration and thus, the transformation can be continuously maintained only with a small amount of cofactor.

Therefore, in one aspect, the present invention provides a method for simultaneously expressing a cofactor regenerating enzyme and a target protein using the cofactor on the cell surface comprising the steps of: (a) preparing a recombinant vector for regenerating the cofactor comprising DNA having a gene encoding an enzyme for regenerating the cofactor linked to a gene encoding a surface anchoring motif so that the enzyme regenerating the cofactor is expressed in the form fused with the surface anchoring motif; (b) preparing a recombinant vector for expressing the target protein comprising DNA having a gene encoding the target protein linked to a gene encoding the surface anchoring motif so that the target protein using the cofactor is expressed in the form fused with the surface anchoring motif; (c) transforming the recombinant vector for expressing the target protein and the recombinant vector for regenerating the cofactor into a host cell; and (d) surface expressing the enzyme regenerating the cofactor and the target protein by culturing the transformed cells.

In the present invention, the surface anchoring motif is preferably selected from the group consisting of membrane proteins, lipoproteins, autotranspoters and S-layer of surface appendage and the membrane protein is preferably selected from the group consisting of outer membrane proteins of *E. coli* including OmpA, Lpp-OmpA, OmpS, LamB, OmpC, PhoE, FadL, OmpC of salmonella and OprF of Pseudomonds.

In the present invention, the host cell is preferably a microorganism and the microorganism is bacteria, including *E. coli* or *Pseudomonas putida*.

In the present invention, the recombinant vector for expression of the target protein and the recombinant vector for regeneration of the cofactor are preferably all compatible.

In the present invention, the cofactor is preferably selected from the group consisting of dehydrogenase coenzyme, transferase coenzyme and isomerase coenzyme and lyase coenzyme. The dehydrogense coenzyme is preferably selected from the group consisting of nicotinamide-adenine-dinucleotide (NAD), nicotinamide-adenine-dinucleotide phosphate (NADP), flavin-mononucleotide (FMN), flavin-adenin-dinucleotide (FAD), cellular hemin and lipoic acid.

In the present invention, the transferase coenzyme is preferably selected from the group consisting of adenosine triphosphate (ATP), phosphoadenyl sulfate (PAPS), uridine diphosphate (UDP), cytidine diphosphate (CDP), guanosine tirphosphate (GTP), inosine triphosphate (ITP), coenzyme A(CoA), tetrahydrofol acid (CoF, $FH_4$), biotin-thiamine pyrophosphate (TPP) and pyridoxal phosphate (PAL) and the isomerase coenzyme and the lyase coenzymes are preferably selected from the group consisting of uridine diphosphate (UDP), pyridoxal phosphate (PAL), thiamine pyrophosphate (TPP) and vitamin $B_{12}$.

In the present invention, the target protein is preferably selected from the group consisting of hormones, hormone analogues, enzymes, enzyme inhibitors, signal transduction proteins or a part thereof, antibodies or a part thereof, single-chain antibodies, binding proteins, binding domains, peptides, antigens, adhesion proteins, structural proteins, regulatory proteins, toxic proteins, cytokine, transcription regulatory factors, blood coagulation factors and plant biodefense-inducing proteins and the enzyme is preferably selected from the group consisting of dehydrogenase, transferase, isomerase and lyase.

In the present invention, the cofactor is nicotinamide-adenine-dinucleotide (NAD), the target protein is lactate dehydrogenase and the cofactor regenerating enzyme is formate dehydrogenase.

In another aspect, the present invention provides a cell transformed with a recombinant vector for regenerating a cofactor comprising DNA having a gene encoding an enzyme regenerating the cofactor linked to a gene encoding a surface anchoring motif and a recombinant vector for expressing a target protein comprising DNA having a gene encoding the target protein using the cofactor linked to a gene encoding a surface anchoring motif, in which the enzyme regenerating the cofactor and the target protein using the cofactor are simultaneously surface-expressed.

In the present invention, the target protein is lactate dehydorgenase and the cofactor regenerating enzyme is pyruvic acid dehydrogenase.

In a preferred embodiment of the present invention, there is provided a method for converting phenylpyruvic acid to (R)-phenyl lactic acid, the method is characterized by using the cell.

EXAMPLES

The present invention will hereinafter be described in further detail by examples. However, it is to be understood that these examples can be modified into other various forms, and the scope of the present invention is not intended to be limited to such examples.

The biotransformation according to the following examples is applied in a single step or multiple steps and in the aqueous solution or non-aqueous solution. The microorganism is used in a mobilized or an immobilized state. Also, it is obvious to a person skilled in the art from the disclosure in the present application that the biotransformation can be performed in combination with other microorganisms or enzymes.

Example 1

Figure 1:
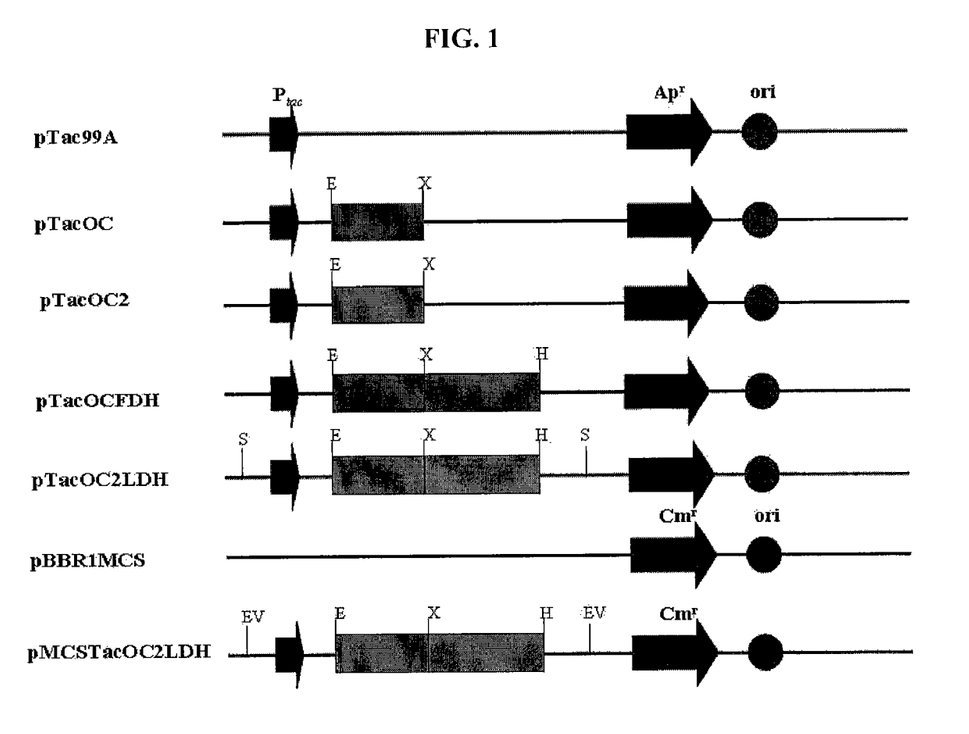
FIG. 1 shows the recombinant plasmid pTacOCFDH and pMCSTacOC2LDH according to the present invention, in which E refers to EcoRI, X refers to XbaI, H refers to HindIII, EV refers to EcoRV, and S refers to SspI.

Preparation of Recombinant Expression Vector (1) Preparation of Surface Expression Vector of Formate Dehydrogenase Gene In order to simultaneously surface express a target protein using a cofactor and an enzyme regenerating the cofactor, a recombinant vector comprising a DNA fragment having the gene of the target protein using the cofactor linked to a surface anchoring motif and a recombinant vector comprising a DNA fragment having the gene encoding the cofactor regenerating enzyme linked to a surface anchoring motif were prepared (FIG. 1).

In order to obtain the surface anchoring motif, PCR was performed using chromosomal DNA of E. coli W3110 (ATCC 27325) as a template and primers of SEQ ID NOs: 1 and 2 to obtain a DNA fragment (Ompc1) comprising a part of the OmpC gene and PCR was performed using primers of SEQ ID NOs: 1 and 3 to obtain a DNA fragment (Ompc2) comprising a part of the Ompc gene (SEQ ID NO: 4).

SEQ ID NO: 1:
5'-cgagctcatgaaagttaaagtactgtcc-3'

SEQ ID NO: 2:
5'-ggctctagagccacgaccgttgttagttacgcc-3'

SEQ ID NO: 3:
5'-ggctctagagccacgacccaggtttttacc-3'

The fragment comprising a part of the OmpC gene was cleaved at the restriction enzyme cleavage site contained in each primer using the restriction enzymes EcoRI and XbaI and the expression plasmid pTac99A (Park and Lee, J. Bacteriol 185:5391) was cleaved using the same restriction enzyme EcoRI and XbaI to obtain a linear vector, which was then ligated with the fragment comprising a part of the OmpC gene to obtain the recombinant plasmids pTacOC and pTacOC2.

As the cofactor regenerating enzyme, formate dehydrogenase capable of regenerating NADH by adding H+ to the cofactor NAD (nicotinamide-adenine-dinucleotide phosphate) was selected using sodium formate as a substrate to obtain formate dehydrogenase (FDH) gene of Hansenula polymorpha.

That is, PCR was performed using chromosomal DNA of Hansenula polymorpha ATCC34438 as a template and primers of SEQ ID NOs: 5 and 6 to obtain a DNA fragment (SEQ ID NO: 7) comprising the FDH gene.

SEQ ID NO: 5:   5'-GCTCTAGAATGAAGGTTGTACTAGTTCTC-3'

SEQ ID NO: 6:   5'-CCCAAGCTTTTATTTGTCGGCACCGTA-3'

In order to confirm the cell surface display of the FDH gene, the DNA fragment comprising the FLAG tag was prepared. PCR was performed using the chromosomal DNA of Hansenula polymorpha ATCC 34438 as a template and a primer of SEQ ID NO: 5 and a primer of SEQ ID NO: 8 comprising FLAG tag to obtain the FDHF(FDH-FLAG tag) fragment comprising the FDH gene containing FLAG tag.

SEQ ID NO: 8:
5'-CCCAAGCTTTTATTTGTCATCGTCGCTTCCTTGTAGTCT

TTGTCGGCACCGTACGA-3'

The FDH fragment and the FDHF fragment were cleaved at the restriction enzyme cleavage site contained in each primer using the restriction enzymes XbaI and HindIII.

The vector pTacOC constructed such that it expresses a part of the cell membrane protein C (OmpC) of E. coli by the tac promoter was cleaved by the restriction enzymes XbaI and HindIII to obtain a linear vector, which was then ligated with the FDH fragment and the FDHF fragment to obtain the recombinant plasmid pTacOCFDH and pTacOCFDHF.

(2) Preparation of Surface Display Vector of Lactate Dehydorgenase Gene

A recombinant plasmid comprising a DNA fragment having a gene encoding lactate dehydrogenase, an enzyme to produce 2 molecules of lactic acid by transferring H+ obtained from NADH to pyruvic acid linked to a gene encoding a cell surface anchoring motif was prepared.

The lactate dehydorgenase (LDH) gene of E. coli was obtained as follows. That is, PCR was performed using a chromosomal DNA of E. coli as a template and primers of SEQ ID NOs: 9 and 10 to obtain a DNA fragment (SEQ ID NO: 11) comprising the LDH gene.

SEQ ID NO: 9:   5'-GCTCTAGAATGAAACTCGCCGTTTATAG-3

SEQ ID NO: 10:   5'-CCCAAGCTTTTAAACCAGTTCGTTCGGGC-3'

In order to confirm the cell surface display of the LDH gene, LDHHis DNA fragment comprising His tag was prepared. PCR was performed using a chromosomal DNA of *E. coli* W3110 as a template with a primer of SEQ ID NO: 9 and a primer of SEQ ID NO: 12 containing a His tag to obtain the LDHHis fragment of LDH gene containing His tag.

```
SEQ ID NO: 12:
5'-CCCAAGCTTTTAATGGTGATGATGGTGATGAACCAG
TTCGTTCGGGCAGG-3
```

The LDH fragment and LDHHis fragment were cleaved at restriction enzyme cleavage sites contained in each primer using the restriction enzymes XbaI and HindIII.

A linear vector obtained by cleaving the vector pTacOC2 constructed such that it expresses a part of the cell membrane protein C (OmpC) of *E. coli* by tac promoter with the same restriction enzymes XbaI and HindIII as the above was ligated with the LDH fragment and the LDHHis fragment to obtain the recombinant plasmids pTacOC2LDH and pTacOC2LDHHis.

When a plurality of plasmids coding different proteins is simultaneously introduced into one host cell, if the replication origins of the plasmids are the same, one of the plasmids survives and the rest disappear. Therefore, plasmids with different replication origins should be used.

Therefore, a linear vector obtained by cleaving pBBR1MCS (Kovach, M. E., et al., gene 166:175, 1995) having a different replication origin from pTacOC with the restriction enzyme EcoRV and treating it with CIP (calf intestinal phosphatase) and the OmpC-LDH fragment obtained by cleaving pTacOC2LDH and pTacOC2LDHHis respectively with the restriction enzyme SspI were ligated to obtain the recombinant plasmids pMCSTacOC2LDH and pMCSTacOC2LDHHis.

Example 2

Preparation of Recombinant *E. coli* Simultaneously Expressing FDH and LDH on the Cell Surface The recombinant plasmids pTacOCFDHF and pMCSTacOC2LDHHis were introduced to *E. coli* XL10-Gold (Tet$^r$ Δ(mcrA)183 Δ(mcrCB-hsdSMR-mrr) 173 endA1 supE44 thi-1 recA1 gyrA96 relA1 lac Hte [F qt proAB lacI$^q$ZΔM15 Tn10 (Tet$^r$) Amy Cam$^r$, Strata gene Cloning System, USA] by electroporation, transformed, and cultured in LB plate supplemented with Ampicillin (50 μg/L) and Chloramphenicol (34 μg/L) to select the transformed strains, thus preparing a transformant XL10-Gold (pTacOCFDHF, pMCSTacOC2LDHHis).

The recombinant plasmid pTacOCFDH and pMCSTacOC2LDH were transformed into *E. coli* XL10-Gold by the same method as the above to prepare a transformant XL10-Gold (pTacOCFDH, pMCSTacOC2LDH).

Also, the recombinant plasmid pTac99A and pBBR1MCS were transformed into *E. coli* XL10-Gold by the same method as the above to prepare a control.

Example 3

Confirmation of Simultaneous Cell Surface Expression by Flow Cytometry

The transformant XL10-Gold (pTacOCFDHF, pMCSTacOC2LDHHis) and the control XL 10-Gold (pTac99A, pBBR1MCS) prepared in Example 2 were inoculated in 10 mL LB medium supplemented with Ampicillin (50 μg/L) and Chloramphenicol (34 μg/L) and cultured at 37□. . When OD at 600 nm was 0.5, 0.1 mM IPTG was added to induce the gene expression. 5 hours after the expression induction of the expression, the culture broth was centrifuged at 4□, 6000 rpm for 5 minutes to recover the cells. The cells were washed with PBS solution (pH 7.2) and re-suspended in the PBS solution containing 2 wt % of BSA (bovine serum albumin). A sample of mouse anti-His serum, a primary antibody only added to the PBS solution containing 2 wt % of BSA in a ratio of 1:1000 and a sample of mouse anti-His serum and mouse anti-FLAG serum added to the PBS solution containing 2 wt % of BSA in a ratio of 1:1000 were reacted at 4° C. for 4 hours. After the reaction, the samples were washed 5 times with PBS solution, and then added with rabbit anti-mouse IgG conjugated with FITC, a secondary antibody in a ratio of 1:200, followed by culturing at 4□ for 12 hours. In order to remove the non-reacted secondary antibody, the samples were washed with PBS solution 5 times and observed on FACS Calibur flow cytometer (Becton Dickinson, USA). The result is shown in FIG. 2.

Figure 2:
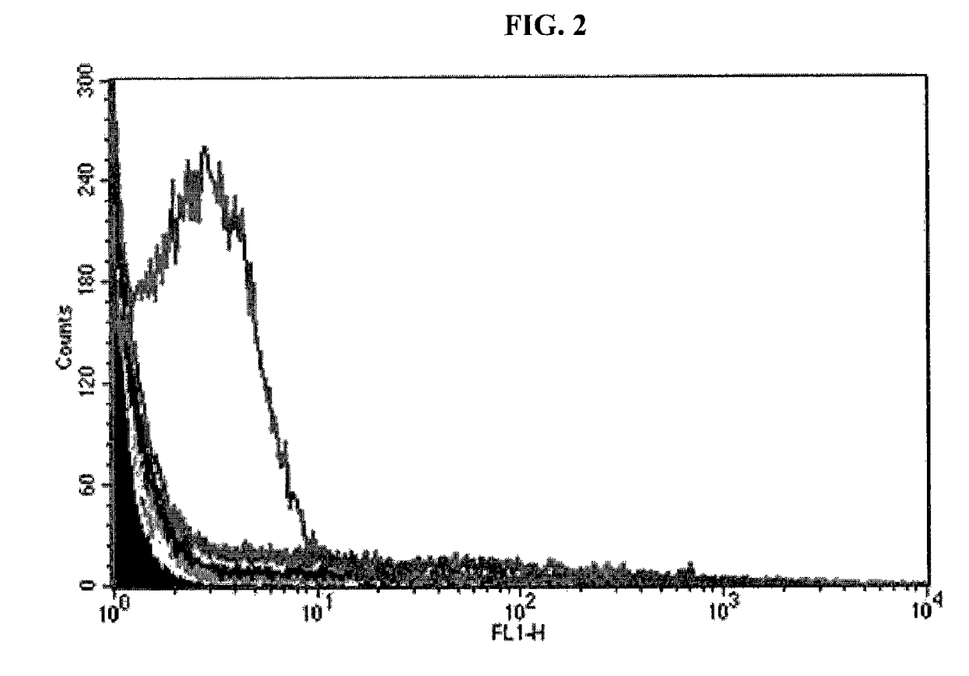
FIG. 2 shows the result of flow cytometry of formate dehydrogenase and lactate dehydrogenase expressed on the cell surface.

The dark area of FIG. 2 refers to the control XL-10 Gold (pTac99A, pBBR1MCS) and the red curve refers to the sample added only with the anti-His serum and the green curve refers to the sample added with both the mouse anti-His serum and the mouse anti-FLAG. From the change in fluorescence, it was confirmed that the two enzymes were simultaneously surface-expressed.

Example 4

Proof of Simultaneous Cell Surface Display Using Immunofluorrescence Microscopy

Figure 3:
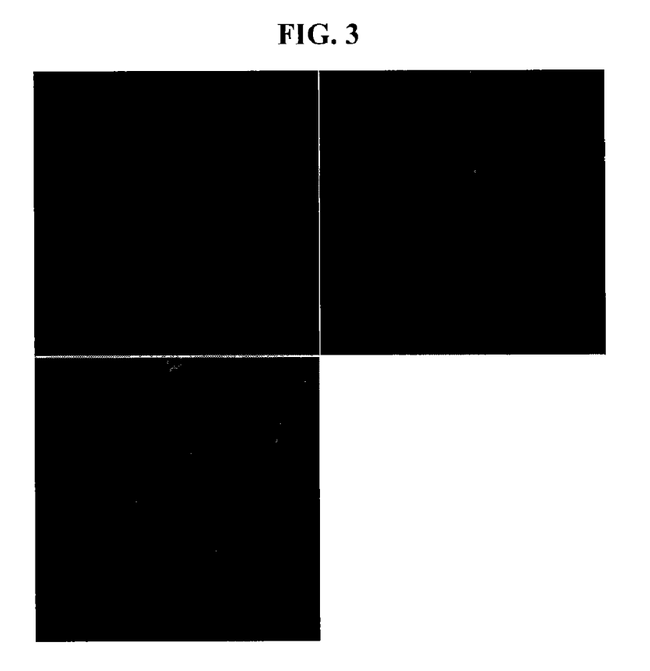
FIG. 3 showed photographs of immunofluorescence microscopy of formate dehydrogenase and lactate dehydrogenase expressed on the cell surface.

The transformants XL10-Gold (pTacOCFDHF, pMCSTacOC2LDHHis) were cultured using the same method as described in Example 3, to induce the expression of the transformed gene. 5 hours after the induction of the expression, the culture broth was centrifuged at 4□, 6000 rpm for 5 minutes to recover the cells. The cells were washed with PBS solution (pH 7.4) and re-suspended in the PBS solution containing 3 wt % of BSA (bovine serum albumin). To the PBS solution containing 3 wt % of BSA, mouse anti-His serum, a primary antibody alone was added in a ratio of 1:1000 and mouse anti-His serum was added together with mouse anti-FLAG serum. The solutions were cultured at room temperature for 1 hour. The culture broth was washed 5 times with PBS solution, treated with Rabbit anti-mouse IgG conjugated with FITC as a secondary antibody in a ratio of 1:1000 and cultured at 4□ for 4 hours. In order to remove non-reacted secondary antibody, each of the culture broth was washed 5 times with PBS solution and observed on the confocal microscope (Carl Zeiss, Jena, Germany). The result is shown in FIG. 3.

The surface expressed formate dehydrogenase and lactate dehydorgenase were shown green and red, respectively. From the result that both green and red were shown, it was noted that the two proteins were simultaneously surface-expressed.

Example 5

Production of Chiral Material Using FDH and LDH Simultaneously Cell Surface-Expressed on *E. coli* XL 10-Gold XL10-Gold (pTacOCFDH, pMCSTacOC2LDH) prepared in Example 2 was inoculated into a 250 ml Erlenmeyer flask containing 100 mL of LB medium supplemented with 100 mL of ampicillin (50 μg/L) and Chloramphenicol (34 μg/L) and cultured at 37° C. for 8 hours. 1 mL of the culture broth was taken and inoculated into a 250 ml Erlenmeyer flask containing 100 mL of LB medium supplemented with 100 mL of ampicillin (50 μg/L) and Chloramphenicol (34 μg/L) and cultured at 37° C. When the absorbance at a wavelength of 600 nm was 0.5, 0.1 mM IPTG was added to induce gene expression. 5 hours after the induction of expression, the culture broth was centrifuged at 4□, 6000 rpm for 5 minutes to recover the cells. The cells were washed with PBS solution (pH 7.2) and lyophilized.

100 mg of the lyophilized, surface expressing *E. coli* was suspended with 100 mg of phenylpyruvic acid, 7 mg of sodium formate and 1.32 mg of NAD in 10 mL of 0.1 M phosphate buffer (pH 7.0) solution and stirred for 48 hours for reaction. After completion of the reaction, the solution was centrifuged at 12,000 rpm for 3 minutes to remove cells and obtain the supernatant. The obtained solution was adjusted to pH 2.0, extracted 5 times with 5 mL of ethyl acetate and subjected to liquid chromatography (column: Chiralcel OD-H; flow rate: 0.5 mL/min; solvent: Hexane/iso-propanol/tri-fluoroacetic acid=80:20:1 (volume); detection: UV 210 nm). As a result, (R)-phenyl lactic acid with an optical purity of 90% or better was obtained.

As described above, The method for transforming a biochemical material according to the present invention can be performed continuously without adding an expensive cofactor in a large amount and thus economical. Also, the microorganism capable of simultaneously surface-expressing at least two target proteins according to the present invention can express a plurality of foreign proteins with normal functions on the cell surface and thus can be used in screening of useful proteins.

While the present invention has been described with reference to the particular illustrative embodiment, it is not to be restricted by the embodiment but only by the appended claims. It is to be appreciated that those skilled in the art can change or modify the embodiment without departing from the scope and spirit of the present invention.

What is claimed is:

1. A method for simultaneously expressing a cofactor regenerating enzyme and a target protein using the cofactor on the cell surface, the method comprising the steps of: (a) preparing a recombinant vector for regenerating the cofactor comprising DNA having a gene encoding an enzyme for regenerating the cofactor linked to a gene encoding outer membrane protein C (OmpC) so that the enzyme regenerating the cofactor is expressed in the form fused with OmpC; (b) preparing a recombinant vector for expressing the target protein comprising DNA having a gene encoding the target protein linked to a gene encoding OmpC so that the target protein using the cofactor is expressed in the form fused with OmpC; (c) transforming the recombinant vector for expressing the target protein and the recombinant vector for regenerating the cofactor into *E. coli*; and (d) surface expressing the enzyme regenerating the cofactor and the target protein by culturing the transformed cell.

2. The method according to claim 1, wherein the recombinant vector for expression of the target protein and the recombinant vector for regeneration of the cofactor are compatible.

3. The method according to claim 1, wherein the cofactor is selected from the group consisting of dehydrogenase coenzyme, transferase coenzyme and isomerase and lyase coenzyme.

4. The method according to claim 3, wherein said dehydrogenase coenzyme is selected from the group consisting of nicotinamide-adenine-dinucleotide (NAD), nicotinamide-adenine-dinucleotide phosphate (NADP), flavin-mononucleotide (FMN), flavin-adenine-dinucleotide (FAD), cellular hemin and lipoic acid.

5. The method according to claim 3, wherein said transferase coenzyme is selected from the group consisting of adenosine triphosphate (ATP), phosphoadenyl sulfate (PAPS), uridine diphosphate (UDP), cytidine diphosphate (CDP), guanosine triphosphate (GTP), inosine triphosphate (ITP), coenzyme A (CoA), tetrahydrofol acid (CoF, $FH_4$), biotin-thiamine pyrophosphate (TPP) and pyridoxal phosphate (PAL).

6. The method according to claim 3, wherein said isomerase and lyase coenzyme is selected from the group consisting of uridine diphosphate (UDP), pyridoxal phosphate (PAL), thiamine pyrophosphate (TPP) and vitamin $B_{12}$.

7. The method according to claim 1, wherein the target protein is selected from the group consisting of hormones, hormone analogues, enzymes, enzyme inhibitors, signal transduction proteins or a part thereof, antibodies or a part thereof, single-chain antibodies, binding proteins, binding domains, peptides, antigens, adhesion proteins, structural proteins, regulatory proteins, toxic proteins, cytokine, transcription regulatory factors, blood coagulation factors and plant biodefense-inducing proteins.

8. The method according to claim 7, wherein the enzyme is selected from the group consisting of dehydrogenase, transferase, isomerase and lyase.

9. The method according to claim 8, wherein the cofactor is nicotinamide-adenine-dinucleotide (NAD) and the target protein is lactate dehydrogenase.

10. The method according to claim 9, wherein the cofactor regenerating enzyme is formate dehydrogenase.

11. The method according to claim 8, wherein the target protein is lactate dehydrogenase.

12. The method according to claim 11, wherein the cofactor regenerating enzyme is pyruvic acid dehydrogenase.

* * * * *